United States Patent
Gao et al.

(10) Patent No.: US 11,773,410 B2
(45) Date of Patent: Oct. 3, 2023

(54) REPAIRING COMPOUND HETEROZYGOUS RECESSIVE MUTATIONS BY ALLELE EXCHANGE

(71) Applicant: University of Massachusetts, Boston, MA (US)

(72) Inventors: Guangping Gao, Westborough, MA (US); Dan Wang, Belchertown, MA (US)

(73) Assignee: University of Massachusetts, Boston, MA (US)

( * ) Notice: Subject to any disclaimer, the term of this patent is extended or adjusted under 35 U.S.C. 154(b) by 191 days.

(21) Appl. No.: 16/093,575

(22) PCT Filed: Apr. 13, 2017

(86) PCT No.: PCT/US2017/027398
§ 371 (c)(1),
(2) Date: Oct. 12, 2018

(87) PCT Pub. No.: WO2017/180859
PCT Pub. Date: Oct. 19, 2017

(65) Prior Publication Data
US 2020/0181651 A1  Jun. 11, 2020

Related U.S. Application Data

(60) Provisional application No. 62/321,799, filed on Apr. 13, 2016.

(51) Int. Cl.
| | |
|---|---|
| *C12N 15/90* | (2006.01) |
| *C12N 9/22* | (2006.01) |
| *C12N 15/10* | (2006.01) |
| *C12N 15/11* | (2006.01) |
| *C12N 15/86* | (2006.01) |

(52) U.S. Cl.
CPC ............ *C12N 15/907* (2013.01); *C12N 9/22* (2013.01); *C12N 15/1024* (2013.01); *C12N 15/11* (2013.01); *C12N 15/86* (2013.01); *C12N 2320/34* (2013.01); *C12N 2750/14143* (2013.01); *C12N 2800/80* (2013.01)

(58) Field of Classification Search
CPC .................................................. C12N 15/907
See application file for complete search history.

(56) References Cited

U.S. PATENT DOCUMENTS

| | | | |
|---|---|---|---|
| 2004/0091923 A1* | 5/2004 | Reyes .................... | C12Q 1/686 435/6.1 |
| 2006/0153826 A1* | 7/2006 | Arnould ................... | C12N 7/00 424/94.61 |

FOREIGN PATENT DOCUMENTS

| | | | | |
|---|---|---|---|---|
| WO | WO-2015089462 A1 * | 6/2015 | ........... | C12N 15/102 |

OTHER PUBLICATIONS

Neuwirth et. al. Interchromosomal Crossover in Human Cells is Associated with Long Gene Conversion Tract. 2007. Molecular and Cellular Biology, vol. 27, No. 15, p. 5261-5274 (Year: 2007).*
Wu et. al. Correction of a Genetic Disease in Mouse via Use of CRISPR-Cas9. 2013. Cell Stem Cell. vol. 13, Issue 6, 5 pp. 659-662 (Year: 2013).*
Richardson and Jasin. Frequent chromosomal translocations induced by DNA double-strand breaks. 2000, vol. 405 pp. 698-700 (Year: 2000).*
Weinstock et al. Modeling oncogenic translocations: Distinct roles for double-strand break repair pathways in translocation formation in mammalian cells. 2006. DNA Repair (5) 1065-1074 (Year: 2006).*
GenBank: AC132619.3. 2003 Mus musculus BAC clone RP23-195N4 from chromosome 7, complete sequence (Year: 2003).*
GenBank: JN963001.1.2011. Mus musculus targeted non-conditional, lacZ-tagged mutant allele Aspa:tm2e(EUCOMM)Wtsi tm1e(EUCOMM)Wtsi) (Year: 2011).*
EP 17783126.0, dated Oct. 8, 2019, Extended European Search Report.
PCT/US2017/027398, dated Jul. 21, 2017, International Search Report and Written Opinion.
PCT/US2017/027398, dated Oct. 25, 2018, International Preliminary Report on Patentability.
Extended European Search Report for International Application No. EP 17783126.0, dated Oct. 8, 2019.
International Search Report and Written Opinion for International Application No. PCT/US2017/027398, dated Jul. 21, 2017.
International Preliminary Report on Patentability for International Application No. PCT/US2017/027398, dated Oct. 25, 2018.
Castellani et al., Consensus on the use and interpretation of cystic fibrosis mutation analysis in clinical practice. J Cyst Fibros. May 2008;7(3):179-96. doi: 10.1016/j.jcf.2008.03.009.
Cleary et al., Phenylketonuria. Paediatrics and Child Heatlh. Mar. 2019;29(3):111-15. Doi: 10.1016/j.paed.2019.01.001.
Iliakis et al., Mechanisms of DNA double strand break repair and chromosome aberration formation. Cytogenet Genome Res. 2004;104(1-4):14-20.
Jamal et al., Keeping CRISPR/Cas on-Target. Curr Issues Mol Biol. 2016;20:1-12. Epub Oct. 10, 2015.
Muller, The Mechanism of Crossing-Over. The American Naturalist. Apr. 1916;50(592):193-221.
Schwank et al., Functional repair of CFTR by CRISPR/Cas9 in intestinal stem cell organoids of cystic fibrosis patients. Cell Stem Cell. Dec. 5, 2013;13(6):653-8. doi: 10.1016/j.stem.2013.11.002.
St-Louis et al., Mutations in the fumarylacetoacetate hydrolase gene causing hereditary tyrosinemia type I: overview. Hum Mutat. 1997;9(4):291-9.

(Continued)

*Primary Examiner* — Samuel C Woolwine
*Assistant Examiner* — Tiffany Nicole Grooms
(74) *Attorney, Agent, or Firm* — Wolf, Greenfield & Sacks, P.C.

(57) ABSTRACT

The disclosure in some aspects relates to methods and compositions for repairing mutations (e.g., compound heterozygous mutations) that are widely found in patients having certain diseases (e.g., monogenic recessive diseases). In some aspects, the disclosure provides a method for targeted allelic exchange using recombinant gene editing complex.

15 Claims, 13 Drawing Sheets

Specification includes a Sequence Listing.

(56) References Cited

OTHER PUBLICATIONS

Wang et al., 733. Somatically Repairing Compound Heterozygous Recessive Mutations by Chromosomal Cut-and-Paste for In Vivo Gene Therapy. Mol Thera. May 1, 2016;24(Supplement 1):S289. Doi: https://doi.org/10.1016/S1525-0016(16)33541-9. 1 page.

Yang et al., A dual AAV system enables the Cas9-mediated correction of a metabolic liver disease in newborn mice. Nat Biotechnol. Mar. 2016;34(3):334-8. doi: 10.1038/nbt.3469. Epub Feb. 1, 2016.

Yoshimi et al., Allele-specific genome editing and correction of disease-associated phenotypes in rats using the CRISPR—Cas platform. Nat Commun. Jun. 26, 2014;5(4240). 11 pages.

Zapotoczny et al., Human Cell Assays for Synthesis-Dependent Strand Annealing and Crossing over During Double-Strand Break Repair. G3 (Bethesda). Apr. 3, 2017;7(4):1191-1199. doi: 10.1534/g3.116.037390.

\* cited by examiner

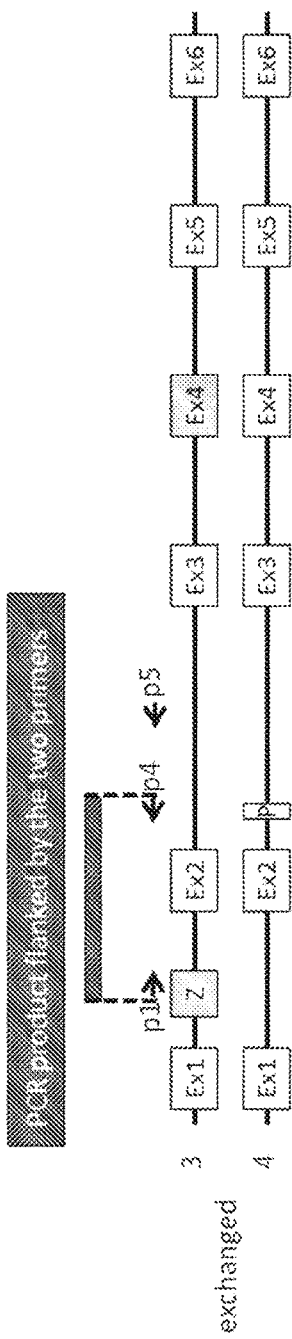

```
                        SEQUENCE LISTING

<160> NUMBER OF SEQ ID NOS: 7

<210> SEQ ID NO 1
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 1
gaggtattgt acaaagatac agaggcagtg atgat                              35

<210> SEQ ID NO 2
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 2
gaggtattgt acacagaggc agtgatgat                                     29

<210> SEQ ID NO 3
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 3
gaggtattgt acaaaagagg cagaggcagt gatgat                             36

<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 4
gactggagcg cacgagac                                                 18

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
gggtgggaaa atagaccaat                                               20
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
aaagagtgga gccttagtgt                                                      20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
ggtattgtac aaagatacag                                                      20
```

REPAIRING COMPOUND HETEROZYGOUS RECESSIVE MUTATIONS BY ALLELE EXCHANGE

RELATED APPLICATIONS

This Application is a national stage filing under 35 U.S.C. § 371 of international patent application number PCT/US2017/027398, filed Apr. 13, 2017, entitled "REPAIRING COMPOUND HETEROZYGOUS RECESSIVE MUTATIONS BY ALLELE EXCHANGE," which claims the benefit of the filing date under 35 U.S.C. 119(e) of U.S. provisional application Ser. No. 62/321,799, filed Apr. 13, 2016, entitled "REPAIRING COMPOUND HETEROZYGOUS RECESSIVE MUTATIONS BY ALLELE EXCHANGE", the entire contents of each of which are incorporated herein by reference.

REFERENCE TO A SEQUENCE LISTING

The instant application contains a Sequence Listing which has been submitted in ASCII format via EFS-Web and is hereby incorporated by reference in its entirety. Said ASCII copy, created on Sep. 28, 2018, is named U012070073US01-SUBSEQ-KZM and is 1 kilobytes in size.

BACKGROUND

Patients affected by monogenic recessive genetic disorders often carry two different mutations of the same gene. The two distinct mutations are located at two positions of the gene, and carried on the two alleles of the gene. This genetic phenomenon is known as compound heterozygosity. Appropriate treatment methods are needed.

SUMMARY

Described herein are methods and compositions useful, in some embodiments, for repairing mutations (e.g., compound heterozygous mutations) that are widely found in patients having certain diseases (e.g., monogenic recessive diseases). Methods described by the disclosure are not limited to a specific gene. Previous gene editing strategy to repair a mutation relies on the delivery of a donor template, whereas methods described by the disclosure utilize the existing normal sequences in a diploid genome to reconstitute a normal gene. In some aspects, the disclosure relates to methods and compositions for targeted allelic exchange.

Accordingly, in some aspects, the disclosure provides a method for targeted allelic exchange, the method comprising contacting a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each chromosome at a site aligning between the positionally unique mutations, such that allelic exchange occurs between the two chromosomes of the pair and produces a mutation-free chromosome and a mutant chromosome.

In some aspects, the disclosure provides a method for targeted allelic exchange, the method comprising delivering to a cell at least one component of a recombinant gene-editing complex, the cell having a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each chromosome at a site aligning between the positionally unique mutations, wherein the gene-editing complex mediates allelic exchange between the two chromosomes of the pair in the cell, producing a mutation-free chromosome and a mutant chromosome.

In some aspects, the disclosure provides a method for targeted allelic exchange in a subject, the method comprising administering to a subject at least one component of a recombinant gene-editing complex, the subject having in a cell a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each chromosome at a site aligning between the positionally unique mutations, wherein the administered gene-editing complex enters the cell and mediates allelic exchange between the two chromosomes of the pair, producing a mutation-free chromosome and a mutant chromosome in the cell.

In some embodiments, the cell is in a subject. In some embodiments, the subject is a mammal, optionally a human. In some embodiments, the subject has or is at risk of having a disease, optionally a monogenic recessive disorder. In some embodiments, the disease is selected from the group consisting of phenylketonuria (PKU), tyrosinemia, lysosomal storage disorder (e.g., Tay-Sachs disease, GM1 gangliosidosis, Sandhoff disease, etc.), a sickle-cell syndrome, Hurler syndrome, Canavan disease, and cystic fibrosis.

In some embodiments, the cell is in vitro or ex vivo. In some embodiments, the subject has or is at risk of having a disease, optionally a monogenic recessive disorder. In some embodiments, the disease is selected from the group consisting of phenylketonuria (PKU), tyrosinemia, lysosomal storage disorder (e.g., Tay-Sachs disease, GM1 gangliosidosis, Sandhoff disease, etc.), a sickle-cell syndrome, Hurler syndrome, Canavan disease, and cystic fibrosis. In some embodiments, the at least one component of the recombinant gene editing complex is administered to a subject by injection.

In some embodiments, the at least one component of the gene editing complex enters the nucleus of the cell.

In some embodiments, each heterogeneous recessive allele is located in a protein-coding region. In some embodiments, each heterogeneous recessive allele is located in a non-coding region, optionally an intron.

In some embodiments, the position of each heterogeneous recessive allele is separated by at least one complete intron. In some embodiments, the complete intron is at least 50 nucleotides in length.

In some embodiments, each heterogeneous allele comprises a polymorphism selected from a single nucleotide polymorphism (SNP), an insertion polymorphism, or a deletion polymorphism. In some embodiments, the polymorphism is associated with a disease, optionally a monogenic recessive genetic disorder. In some embodiments, the disease is selected from the group consisting of phenylketonuria (PKU), tyrosinemia, lysosomal storage disorder (e.g., Tay-Sachs disease, GM1 gangliosidosis, Sandhoff disease, etc.), a sickle-cell syndrome, Hurler syndrome, Canavan disease, and cystic fibrosis.

In some embodiments, the site aligning between the positionally unique mutations is located in a non-coding region, optionally an intron.

In some embodiments, the recombinant gene editing complex comprises a Cas protein, a zinc finger nuclease (ZFN), a Transcription activator-like effector nuclease (TALEN), or a meganuclease (e.g., Meganuclease I-SceI). In some embodiments, the Cas protein is a Cas9 protein, a Cpf1 protein, or a variant thereof. In some embodiments, the recombinant gene editing complex further comprises a guide RNA (gRNA), optionally a single-stranded guide RNA (sgRNA).

In some embodiments, the allelic exchange occurs via non-homologous end-joining (NHEJ) or homology directed repair (HDR).

In some embodiments of methods described by the disclosure, at least one component of a gene editing complex is delivered to the cell or delivered to the subject in a recombinant adeno-associated virus (rAAV).

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing.

FIG. 3A shows two alleles that are compound heterozygous for the lacZ mutation (Z) and Nur7 or KO mutation (Ex4). DSBs induced by Cas9 are shown as lightning bolts. Primer 1 (p1) binds to the lacZ insertion, p2 binds to a loxP site (P) in intron 2, and p5 binds to a region shared by all three alleles. In the first round of nested PCR, primers p1 and p5 amplify both the original allele 1 and the exchanged allele 3. In the second round of nested PCR, primers p1 and p4 amplify only the exchanged allele. FIG. 3B shows recombinant AAV vectors expressing SpCas9 (top) and sgRNA targeting a site between exon 2 and a loxP site (bottom).

FIGS. 5A-5C show allele exchange in mouse tissue (e.g., mouse liver). FIG. 5A shows the result of the $2^{nd}$ round of nested PCR as described in FIG. 3A. The arrow points to a positive band of predicted size (1.1 kb). The designation "7" or "KO" indicates the other original allele in addition to the lacZ allele. Each lane represents an individual mouse. FIG. 5B shows TOPO sequencing identified PCR products that harbor the sequences of p1 and p4, present only in exchanged allele 3 (e.g., exchanged allele having both mutations). FIG. 5C shows TOPO sequencing identified indel mutations at predicted SpCas9 cleavage site, namely 3 bp upstream of PAM sequence; SEQ ID NOs: 1, 2, 3 and 3 are found from top to bottom, respectively.

FIG. 6A shows the GT construct (half GFP-intron-tdTomato without ATG; top) or the TG construct (ATG-intron-half GFP; bottom) that is carried on the same locus of Chromosome 11. Both constructs share the same intronic sequence containing a loxP site (P). CAG: CAG promoter; lightning: sgIntron target site. FIG. 6B shows fluorescence signal of GFP and tdTomato in cryo-sections of liver and heart of 6-week-old GT/TG mice treated by tail vein injection with rAAV9.CB6-PI-Cre (Cre) at 2E12 genome copies (GC), or rAAV9.u1a-SpCas9 combined with rAAV9.u6-sgIntron (Cas9+sgIntron) at 1E12 GC of each vector. N=3 or 4 mice.

FIG. 7A shows fluorescence signal of GFP and tdTomato in cryo-sections of liver and heart of neonatal (postnatal day 1, P1) GT/TG mice treated by facial vein injection with rAAV9.CB6-PI-Cre (Cre) at 4E11 genome copies (GC), or rAAV9.u1a-SpCas9 combined with rAAV9.u6-sgIntron (Cas9+sgIntron) at 2E11 GC of each vector. N=3 or 5 mice. FIG. 7B shows representative microscopic images showing the GFP and tdTomato (tdT) fluorescence in liver and heart tissue sections from two mice. NoTx: mouse with no treatment; SpCas9+sgRNA: mouse treated with rAAV-SpCas9 and rAAV-sgRNA at postnatal day 1 (P1). These mice were examined at 5 weeks old. FIG. 7C shows quantification of GFP and tdT fluorescence signal in liver and heart tissue sections obtained from all experimental mice (n=5 per group). Horizontal lines depict the average values of five samples within each group. Left panel: mice were treated on P1, and examined at P35. Right panel: mice were treated at six weeks old, and examined at 11 weeks old. FIG. 7D shows an alignment of 12 reads representing the GG allele obtained from SMRT sequencing. A, C, G, and T are color-coded, but individually indistinguishable on this collapsed view. The sequence identity is labelled at top (drawn to scale). P: CAG promoter.

FIG. 8A shows a schematic representation of the genomic structure of the $Fah^{\Delta E5}$ and $Fah^{PM}$ alleles and strategy to induce allelic exchange (drawn to scale). Exons 5 to 9 are labeled. Bar at exon 5 denotes location for insertion of a neomycin cassette; Line in exon 8 represents a G→T mutation; Lightning: Cas9/sgRNA target site. FIG. 8B shows representative images of Fah immunohistochemistry (IHC) in liver sections from a mouse treated with rAAV-SpCas9 and rAAV-sgAspa (ctrl hereafter), and a mouse treated with rAAV-SpCas9 and rAAV-sgFah (sgFah hereafter). Mice were treated at P1, maintained on NTBC water, and euthanized at P35. Boxed areas are enlarged and shown to visualize the Fah-positive cells (dark staining). FIG. 8C shows an agarose gel image showing the detection of reverse-transcription (rt) PCR products of Fah messenger RNA in liver lysate. M: DNA marker, sizes in base pairs (bp) are labelled; Lane 1: Wild-type (WT) mouse; Lane 2: Homozygous ΔE5 mouse; Lane 3: Homozygous PM mouse; Lanes 4, 5: Compound heterozygous (comp het) mice treated with ctrl rAAV at P1; Lanes 6, 7: Comp het mice treated with sgFah rAAV at P1. All mice were euthanized at P35. Top arrowhead: product encompassing exons 5 to 9 with no mutation; Bottom arrowhead: product missing exon 8 due to the G→T mutation in the $Fah^{PM}$ allele. A representative Sanger sequencing chromatogram is shown at bottom, revealing the junction between exon 8 and exon 9 (SEQ ID NO: 4) in the rt-PCR product (top arrowhead) of lane 6. FIG. 8D shows body weight curves after NTBC withdrawal on P35. The body weight measured immediately prior to NTBC withdrawal was set as 100%, and relative weight in percentage over time was measured daily until euthanasia. Left panel: mice treated with ctrl rAAV; Right panel: mice treated with sgFah rAAV; N=5 per group. FIG. 8E shows representative images of Fah IHC in liver sections from a mouse treated with ctrl rAAV, and a mouse treated with sgFah rAAV. These mice were treated at P1, maintained on NTBC water until P35, and since then fed with regular water until euthanasia. Note that the Fah-positive cells in the sgFah liver appear to cluster in islands, consistent with clonal expansion. FIG. 8F shows neighboring liver sections were used in Fah IHC and hematoxylin and eosin (HE) staining. Note that the Fah-positive cells (dark staining in IHC) appear histologically normal as assessed by HE. FIG. 8G shows serum aspartate transaminase (AST) (top panel) and alanine transaminase (ALT) (bottom panel) levels in WT mice and comp het mice treated with ctrl rAAV or sgFah rAAV. Each dot represents one mouse. Horizontal lines depict the average values. One-way ANOVA was performed (p<0.001, not shown), followed by multiple comparisons. **: p<0.01; *: p<0.05, compared to the ctrl group after adjusted for multiple comparisons.

FIG. 9A shows a schematic depiction of circularization PCR showing allelic exchange at the DNA level. Liver genomic DNA was digested with restriction enzymes (RE) SphI (light gray arrowhead) and ScaI (dark gray arrowhead). This digestion generates unique DNA fragments from four Fah alleles, namely the original $Fah^{\Delta E5}$ and $Fah^{PM}$ alleles, and the $Fah^{\Delta E5-PM}$ and $Fah^{WT}$ alleles resulting from allelic exchange (not drawn to scale). Only exon 5 and exon 8 are labelled (dark gray boxes). The other genomic sequence is shown as light gray bar. Bar at exon 5: neo insertion; Bar at exon 8: G→T mutation. The fragmented DNA ends were blunted, and individual DNA fragment underwent circularization by self-ligation. The resulting circular DNA was subjected to PCR using primers binding to common sequences present in all four Fah alleles (black arrows). PCR products were cloned into a TOPO vector, and the identity of amplicon in individual clones was determined by Sanger sequencing. FIG. 9B shows a stacked histogram showing the number of reads obtained from TOPO sequencing as shown in FIG. 9A. Each bar represents one mouse, either treated with ctrl rAAV and euthanized due to −20% body weight loss after NTBC withdrawal (ctrl), or treated with sgFah rAAV and euthanized after initial body weight loss due to NTBC withdrawal was rescued. TOPO reads indicative of different Fah alleles are shaded differently.

DETAILED DESCRIPTION

Figure 1:
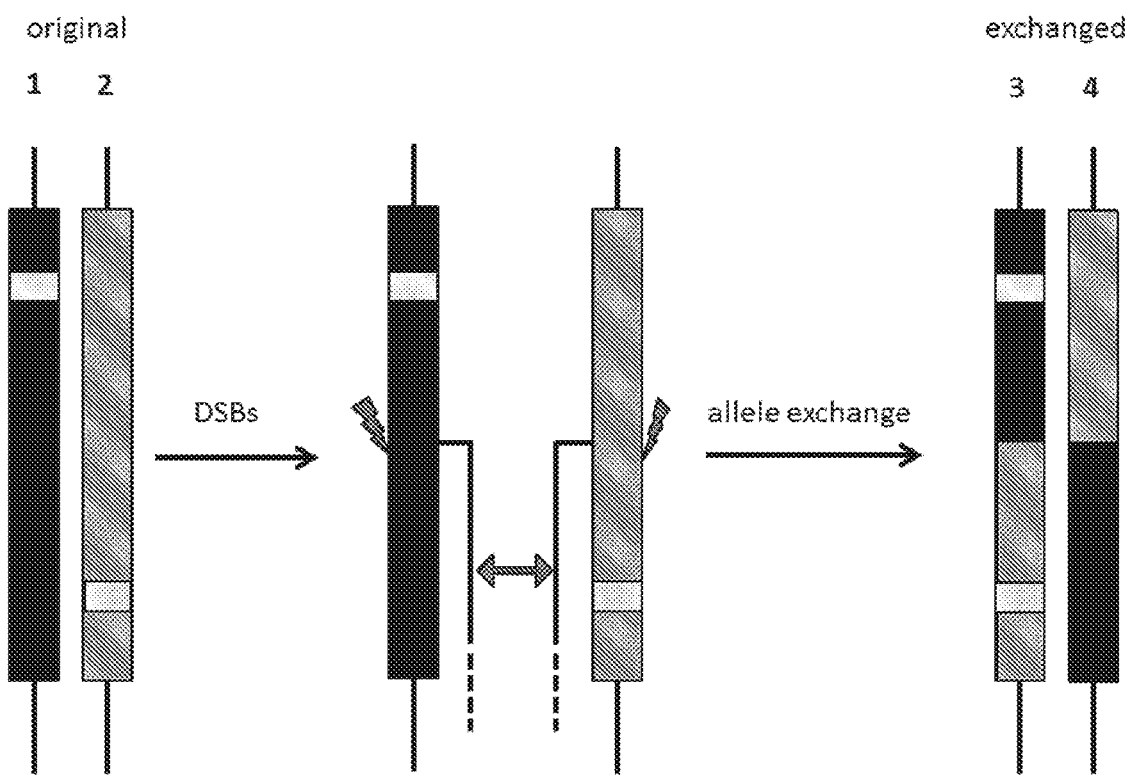
FIG. 1 shows the repair of compound heterozygous mutations by allelic exchange. Each of the two original alleles (1 and 2, black and dark gray bars) carries a mutation (light shaded boxes). Targeted DNA double-stranded breaks (DSBs) at a site between the two mutations are induced by a nuclease (lightning bolts). The homologous chromosomes exchange genetic material (e.g., DNA; double-headed arrows), at the break points. The exchanged alleles (3 and 4) are a mixture of the original alleles (1 and 2). Allele 3 carries two mutations (e.g., both heterozygous mutations; light shaded boxes) and allele 4 is mutation-free.

Gene editing technology is useful for repairing particular DNA mutations and provides an avenue for personalized medicine. In essence, gene editing takes place in two steps: inducing targeted DNA double-stranded breaks (DSBs) by nucleases such as Cas9, and repairing the DSBs by the error-prone non-homologous end joining (NHEJ) pathway or the precise homology-directed repair (HDR) pathway. The current pre-clinical development of gene editing technology for therapeutic use can be generally categorized into two strategies: gene disruption that is protective (e.g., CCR4 disruption for HIV protection) and precise repairing of a known mutation. The gene disruption strategy takes advantage of the error-prone NHEJ, and was used in ex vivo gene therapy, but so far has not been demonstrated for in vivo use. The efficacy of precise repairing in vivo is limited by the low frequency of HDR with a repair template.

Aspects of the disclosure relate to methods and compositions for repairing mutations (e.g., compound heterozygous mutations) that are associated with certain diseases (e.g., monogenic recessive diseases). In some aspects, the disclosure relates to the discovery that gene editing complexes (e.g., CRISPER/Cas system) can be engineered to cause double stranded breaks (DSBs) in the DNA of a subject at specific positions of a pair of homologous nucleic acids (e.g., homologous chromosomes that are compound heterozygous at a particular allele) that results in allelic exchange between the pair of homologous nucleic acids.

In some aspects, the disclosure provides a method for targeted allelic exchange, the method comprising delivering to a cell at least one component of a recombinant gene-editing complex, the cell having a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each chromosome at a site aligning between the positionally unique mutations, wherein the gene-editing complex mediates allelic exchange between the two chromosomes of the pair in the cell, producing a mutation-free chromosome and a mutant chromosome.

As used herein, "targeted allelic exchange" refers to the physical transfer of genetic information (e.g., a nucleic acid encoding a particular gene allele, or portion of a gene allele) between two nucleic acids (e.g., nucleic acids located on chromosomes) at a specific, user-defined locus. Allelic exchange can occur between two homologous nucleic acids, or two heterologous (e.g., unrelated) nucleic acid. In some embodiments of methods described by the disclosure, allelic exchange occurs on a chromosome or between a pair of chromosomes. In some embodiments, the chromosome is chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, chromosome 16, chromosome 17, chromosome 18, chromosome 19, chromosome 20, chromosome 21, chromosome 22, or an X chromosome. In some embodiments, allelic exchange occurs between heterologous chromosomes (e.g., chromosome 1 and chromosome 8). However, generally, methods described by the disclosure relate to allelic exchange between homologous chromosomes. As used herein, "homologous chromosomes" refers to a pair of chromosomes that each carry the same genes in the same order. For example, maternal chromosome 12 and paternal chromosome 12 of a human both contain the gene encoding phenylalanine hydroxylase at position 23.2. However, it should be appreciated that the alleles for each gene carried by homologous chromosomes are not always identical (e.g., each allele may be polymorphic at a given location). In some embodiments, allelic exchange is achieved by non-homologous end-joining (NHEJ) or homology directed repair (HDR).

Heterologous Recessive Alleles

In some embodiments each chromosome of a pair of homologous chromosomes has a heterogeneous recessive allele of the same gene. As used herein, "heterogeneous recessive allele" refers to different (e.g., different with respect to a corresponding homologous chromosome), alleles (e.g., gene variants, or polymorphs) that cause a similar variant phenotype when present in a heterozygous state. A subject that has a pair of homologous chromosomes each having a heterogeneous recessive allele of the same gene is, in some embodiments, referred to "compound heterozygous" for that particular gene.

In some embodiments, a heterogeneous allele comprises a mutation. A "mutation" refers to polymorphism at a locus of a gene that results in a "mutant" allele having a different nucleic acid sequence than the nucleic acid sequence of the wild-type (e.g., non-mutant) allele. As used herein, "polymorph" or "polymorphism" refers to variation in the nucleotide sequence at a specific position of a gene. Examples of nucleic acid polymorphism include single nucleotide polymorphism, insertion polymorphism, and deletion polymorphism. As used herein, "single nucleotide polymorphism" (SNP) refers to a polymorphism where each allele differs by the replacement of a single nucleotide in the DNA sequence of the allelic gene at a specific position. For example, at a given position of a gene, a wild-type nucleotide (e.g., A, C, G, or T) is substituted by a variant nucleotide (e.g., A, C, G, or T) such that the wild-type nucleotide and the variant nucleotide are not the same nucleotide base at that position. In some embodiments, a single nucleotide change can alter the structure and function of the corresponding gene product (e.g., a protein). In some embodiments, a SNP does not alter the structure or function of the corresponding gene product (e.g., a silent mutation or synonymous mutation).

An "insertion polymorphism" refers to a polymorphism were the variant allele contains an insertion of nucleotides at a specific position relative to the same position of a wild-type allele. An insertion polymorphism can range from about 1 nucleotide to about 5000 nucleotides in length. In some embodiments, an insertion polymorphism ranges from about 1 nucleotide to about 10 nucleotides in length. In some embodiments, an insertion polymorphism ranges from about 5 nucleotides to about 100 nucleotides in length. In some embodiments, an insertion polymorphism ranges from about 50 nucleotides to about 500 nucleotides in length. In some embodiments, an insertion polymorphism ranges from about 100 nucleotides to about 1000 nucleotides in length. In some embodiments, an insertion polymorphism ranges from about 500 nucleotides to about 2500 nucleotides in length. In some embodiments, an insertion polymorphism ranges from about 1000 nucleotides to about 5000 nucleotides in length. In some embodiments, an insertion polymorphism is more than 5000 nucleotides in length (e.g., 6000, 7000, 8000, 9000, 10000, or more nucleotides in length. In some embodiments, an insertion polymorphism alters the structure and function of the corresponding gene product (e.g., a protein). In some embodiments, an insertion polymorphism results in a non-functional gene product (e.g., a protein). In some embodiments, an insertion polymorphism does not alter the structure or function of a gene product (e.g., a protein).

A "deletion polymorphism" refers to a polymorphism were the variant allele contains an deletion of nucleotides at a specific position relative to the same position of a wild-type allele. A deletion polymorphism can range from about 1 nucleotide to about 5000 nucleotides in length. In some embodiments, a deletion polymorphism ranges from about 1 nucleotide to about 10 nucleotides in length. In some embodiments, a deletion polymorphism ranges from about 5 nucleotides to about 100 nucleotides in length. In some embodiments, a deletion polymorphism ranges from about 50 nucleotides to about 500 nucleotides in length. In some embodiments, a deletion polymorphism ranges from about 100 nucleotides to about 1000 nucleotides in length. In some embodiments, a deletion polymorphism ranges from about 500 nucleotides to about 2500 nucleotides in length. In some embodiments, a deletion polymorphism ranges from about 1000 nucleotides to about 5000 nucleotides in length. In some embodiments, a deletion polymorphism is more than 5000 nucleotides in length (e.g., 6000, 7000, 8000, 9000, 10000, or more nucleotides in length. In some embodiments, a deletion polymorphism alters the structure and function of the corresponding gene product (e.g., a protein). In some embodiments, a deletion polymorphism results in a non-functional gene product (e.g., a protein). In some embodiments, a deletion polymorphism does not alter the structure or function of a gene product (e.g., a protein).

In some embodiments, each heterogeneous recessive allele has a positionally unique mutation (e.g., polymorphism). As used herein, "positionally unique mutation" refers to a polymorphism that is spatially distinct from the mutation (e.g., polymorphism) on the corresponding heterologous nucleic acid (e.g., heterologous chromosome). For example, a subject that is compound heterozygous for the ASPA gene may have one copy of the gene containing a T728G mutation and a second allele of the ASPA gene containing a "T" at position 728 and having a T902C mutation; in this example, the T728G and T902C mutations are "positionally unique". A positionally unique mutation can be located in a protein-coding region (e.g., an of a gene) or in a non-coding region. Examples of non-coding regions include but are not limited to an intron, regulatory element (e.g., cis-regulatory element or trans-regulatory element), promoter, untranslated region (UTR), pseudogene, transposon or retrotransposon, and telomere.

In some embodiments, positionally unique mutations of heterogeneous recessive alleles are separated by at least one complete intron. A "complete" intron refers to a nucleotide sequence containing 5' and 3' splice sites, a branch site, and a non-random, conserved nucleotides flanking both the 5' and 3' splice sites. In some embodiments, a complete intron is at least 50 nucleotides in length. In some embodiments, a complete intron ranges from about 50 nucleotides to about 10,000 nucleotides in length. In some embodiments, positionally unique mutations of heterogeneous recessive alleles are separated by between about 50 and about 10,000 nucleotides. In some embodiments, positionally unique mutations of heterogeneous recessive alleles are separated by between about 100 and about 5,000 nucleotides. In some embodiments, positionally unique mutations of heterogeneous recessive alleles are separated by between about 1000 and about 2,500 nucleotides. In some embodiments, positionally unique mutations of heterogeneous recessive alleles are separated by between about 2000 and about 8000 nucleotides (e.g., about 2000, about 3000, about 4000, about 5000, about 6000, about 7000, or about 8000 nucleotides).

In some cases, mutations (e.g., polymorphisms) result in aberrant (or lack of) gene product (e.g., protein) function and are associated with disease. In some embodiments, the disease is a monogenic recessive disease. A "monogenic recessive disease" is a disease that is characterized by a defect in a single gene (e.g., a defect in a single protein) and is present only when a subject is compound heterozygous for the gene with which the disease is associated (e.g., carries two different mutated alleles of the same disease-associated gene). Examples of monogenic recessive diseases include but are not limited to phenylketonuria (PKU), tyrosinemia, Tay-Sachs disease, a sickle-cell syndrome, Hurler syndrome, Canavan disease, and cystic fibrosis.

In some embodiments, the monogenic recessive disease is a lysosomal storage disorder. Lysosomal storage disorders (also referred to as Lysosomal storage diseases) are a group of inherited metabolic disorders that result from defects in lysosomal function. Generally, lysosomal storage diseases are characterized by impaired function of a single protein (e.g., enzyme) involved in lysosomal metabolism. For example, Tay-Sachs disease is caused by a genetic mutation in the hexosaminidase A (HEXA) gene and results in the inability of the HEXA enzyme to hydrolyze GM2 gangliosides. Other examples of lysosomal storage diseases and their associated proteins include but are not limited to Aspartylglucosaminuria (Aspartylglucosamininidase), Infantile Batten disease (Palmitoyl protein thioesterase), Late infantile Batten disease (tripeptidyl peptidase), Fabry disease (α-Galactosidase), Fucosidosis (α-Fucosidase), Galactosialidosis (Protective protein/cathepsin A), Gaucher disease (β-Glucosidase), Galactosialidosis (Protective Protein/Cathepsin A), Globoid-cell leukodystrophy (Galactosylceramidase), GM1 gangliosidosis (β-Galactosidase), α-Mannosidosis (α-Mannosidase), Metachromatic leukodystrophy (Arylsulfatase A), Mucopolysaccharidosis I (α-L-Iduronidase), Mucopolysaccharidosis II (iduronate sulfatase), Mucopolysaccharidosis IIIA (Heparin Sulfatase), Mucopolysaccharidosis IIIB (α-N-acetylglucosaminidase), Mucopolysaccharidosis IIIC (acetyl-CoA alpha glucosaminide acetyltransferase), Mucopolysaccharidosis IIID (N-acetylglucosamine-6-sulfate sulfatase), Mucopolysaccharidosis IVA (N-acetylgalactosamine 6-sulfatase), Mucopolysaccharidosis IVB (β-Galactosidase), Mucopolysaccharidosis IX (hyaluronidase), Mucopolysaccharidosis VI (Arylsulfatase B), Mucopolysaccharidosis VII (β-Glucuronidase), Mucolipidosis type I (α-neuraminidase), Mucolipidosis type II (GlcNAc-1-phosphotransferase), Mucolipidosis type III (N-acetylglucosamine-1-phosphotransferase), Nieman-Pick disease (Acid sphingomyelinase), Pompe disease (α-Glucosidase), Sandhoff disease (β-Hexosaminidase A and B) Schindler disease (α-N-acetylgalactosaminidase), Tay-Sachs disease (β-Hexosaminidase A), and Wolman disease (Acid lipase).

Gene Editing Complexes

Aspects of the disclosure relate to the discovery that gene editing complexes can mediate allelic exchange between heterogeneous recessive alleles having positionally unique mutations. As used herein, "gene editing complex" refers to a biologically active molecule (e.g., a protein, one or more proteins, a nucleic acid, one or more nucleic acids, or any combination of the foregoing) configured for adding, disrupting or changing genomic sequences (e.g., a gene sequence) by causing a double stranded break (DSB) in a target DNA. Examples of gene editing complexes include but are not limited to Transcription Activator-like Effector Nucleases (TALENs), Zinc Finger Nucleases (ZFNs), engineered meganuclease re-engineered homing endonucleases, the CRISPR/Cas system, and meganucleases (e.g., Meganuclease I-SceI). In some embodiments, a gene editing complex comprises proteins or molecules (e.g., components) related to the CRISPR/Cas system, including but not limited to Cas9,Cas6, dCas9, CRISPR RNA (crRNA), trans-activating crRNA (tracrRNA), and variants thereof. In some embodiments, the Cas protein is a Cpf1 protein, or a variant thereof.

As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), meganucleases (e.g., engineered meganucleases) and CRISPR-associated proteins (Cas nucleases). In some embodiments, the nuclease is a ZFN. In some embodiments, the ZFN comprises a FokI cleavage domain. In some embodiments, the ZFN comprises $Cys_2His_2$ fold group. In some embodiments, the nuclease is a TALEN. In some embodiments, the TALEN comprises a FokI cleavage domain. In some embodiments, the nuclease is a meganuclease.

Examples of meganucleases include but are not limited to I-SceI, I-CreI, I-DmoI, and combinations thereof (e.g., E-DreI, DmoCre).

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9,Cas6 and dCas9. dCas9 is an engineered Cas protein that binds to a target locus but does not cleave said locus. In some embodiments, the nuclease is Cas9. In some embodiments, the Cas9 is derived from the bacteria S. pyogenes (SpCas9).

For the purpose of genome editing, the CRISPR system can be modified to combine the tracrRNA and crRNA in to a single guide RNA (sgRNA) or just (gRNA). As used herein, the term "guide RNA" or "gRNA" refers to a polynucleotide sequence that is complementary to a target sequence in a cell and associates with a Cas nuclease, thereby directing the Cas nuclease to the target sequence. In some embodiments, a gRNA ranges between 1 and 30 nucleotides in length. In some embodiments, a gRNA ranges between 5 and 25 nucleotides in length. In some embodiments, a gRNA ranges between 10 and 20 nucleotides in length. In some embodiments, a gRNA ranges between 14 and 18 nucleotides in length. In some embodiments, the recombinant gene editing complex further comprises a guide RNA (gRNA), optionally a single-stranded guide RNA (sgRNA). In some embodiments, a gRNA or sgRNA is complementary to SEQ ID NO: 5, 6 or 7.

In some embodiments, one or more components of a gene editing complex that are grafted to an AAV (e.g., AAV2) capsid protein, VP2. However, in some embodiments, the same strategy can be applied in other contexts. For example, the SpCas9 can be replaced with any modified SpCas9 such as mutated or truncated forms, Cas9 proteins from other species and nucleases used in other gene editing platforms such as ZFNs and TALENs. In some embodiments, a nuclease terminally grafted to an AAV2 capsid protein may also be fused to another functional domain, for example single guide RNA (sgRNA). In some embodiments, one or more components of a gene editing complex can be encoded by a nucleic acid located within an rAAV vector (e.g., the gene editing complex is a transgene located within an rAAV vector). In some embodiments, one component of a gene editing complex (e.g., Cas9) is grafted onto an AAV (e.g., AAV2) VP2 capsid protein and a second component of the gene editing complex (e.g., a gRNA or sgRNA) is located within an rAAV vector (e.g., as a transgene within the rAAV vector). It should also be appreciated that one or more components of a gene editing complex can be located on (or within) a plasmid (e.g., a bacterially-derived plasmid) or a viral vector (e.g., a retroviral vector).

In some embodiments, the allelic exchange occurs via non-homologous end-joining (NHEJ) or homology directed repair (HDR). As used herein, "non-homologous end-joining" refers to refers to a cellular process in which a double stranded DNA break (DSB) is repaired by the direct joining of two non-homologous DNA segments (see, e.g., Cahill et al. (2006), *Front. Biosci.* 11:1958-1976). As used herein, "homology directed repair" refers to a cellular process in which a DSB is repaired by the joining of a homologous "donor" nucleic acid to patch a DSB in a "template" nucleic acid (e.g., the nucleic acid having the DSB). Generally, DNA repair occurs in the nucleus of a cell. Therefore, in some embodiments, the at least one component of the gene editing complex enters the nucleus of the cell.

In some aspects, the disclosure relates to the discovery that location-specific cleavage of homologous chromosomes having heterogeneous recessive alleles (e.g., inducing DSBs) results in allelic exchange between the homologous chromosomes and production of a mutation-free chromosome and a mutant chromosome. In some embodiments, the location-specific cleavage (e.g., the DSB) occurs at a site aligning between the positionally unique mutations. As used herein "site aligning between positionally unique mutations" refers to a site on each nucleic acid of a pair (e.g., a nucleic acid on each of a pair of homologous chromosomes) that is flanked by the loci of the positionally unique mutations when the nucleic acids (e.g., chromosomes) are substantially aligned. For example, in a pair of homologous chromosomes where one allele has a mutation at position 1 and one allele has a mutation at position 10, a site aligning between the positionally unique mutations is a site at a site between position 1 of the allele and position 10 of the allele (e.g., position 2, 3, 4, 5, 6, 7, 8, or 9 of the allele). A non-limiting example of a site aligning between positionally unique mutations is depicted by the lightning bolts in the center of FIG. 1. In some embodiments, the site aligning between the positionally unique mutation is located in a non-coding region. Examples of non-coding regions include but are not limited to introns, regulatory elements (e.g., cis-regulatory element or trans-regulatory element), promoters, untranslated regions (UTRs), pseudogenes, transposons or retrotransposons, and telomeres.

As used herein, "mutation-free chromosome" refers to a chromosome characterized by a non-mutant allele (e.g., a wild-type allele) of a particular disease-associated mutation (e.g., a mutation or polymorphism associated with a monogenic recessive disease). As used herein, a "mutant chromosome" refers to a chromosome characterized by the presence of at least two mutant alleles (e.g., polymorphs) of a particular disease-associated mutation (e.g., a mutation or polymorphism associated with a monogenic recessive disease). A non-limiting example of a mutation free chromosome and a mutant chromosome is depicted in the right side of FIG. 1.

Recombinant AAVs

In some aspects, the disclosure relates to the delivery of at least one component of a gene editing complex to a cell. In some embodiments, the at least one component of a gene editing complex is delivered to a cell using an isolated recombinant adeno-associated virus (rAAV).

As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner. In some embodiments, a terminally grafted nuclease (e.g., at least one component of a gene editing complex) is present on all three capsid proteins (e.g., VP1, VP2, VP3) of a rAAV. In some embodiments, the terminally grafted nuclease is present on two of the capsid proteins (e.g., VP2 and VP3) of a rAAV. In some embodiments, the terminally grafted nuclease is present on a single capsid protein of a rAAV. In some embodiments, the terminally grafted nuclease is present on the VP2 capsid protein of the rAAV.

In some aspects, the instant disclosure relates to the location within an AAV capsid protein where a nuclease (e.g., at least one component of a gene editing complex) is grafted. In some embodiments, the nuclease (e.g., at least one component of a gene editing complex) is N-terminally grafted to the capsid protein. In some embodiments, the nuclease (e.g., at least one component of a gene editing complex) is C-terminally grafted to a capsid protein. In some embodiments, a nuclease (e.g., at least one component of a gene editing complex) that is C-terminally grafted to a capsid protein (e.g., VP2) resides within the viral particle, and the viral particle does not contain a genome, e.g., a nucleic acid harboring a transgene.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art. The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein.

The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

The foregoing methods for packaging recombinant vectors in desired AAV capsids to produce the rAAVs of the disclosure are not meant to be limiting and other suitable methods will be apparent to the skilled artisan.

Recombinant AAV Vectors

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., gRNA or sgRNA) or other gene product, of interest. In some embodiments, the transgene encodes at least one component of a gene editing complex, such as a gRNA or a sgRNA. In some embodiments, the nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc..) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

Therapeutic Uses

In some aspects, the disclosure provides methods and compositions for the treatment of diseases associated with heterogeneous recessive alleles, such as monogenic recessive disorders. Accordingly, in some embodiments, the disclosure provides a method for targeted allelic exchange, the method comprising delivering to a cell at least one component of a recombinant gene-editing complex, the cell having a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each chromosome at a site aligning between the positionally unique mutations, wherein the gene-editing complex mediates allelic exchange between the two chromosomes of the pair in the cell, producing a mutation-free chromosome and a mutant chromosome.

Methods and compositions described by the disclosure are useful, in some embodiments, for targeted allelic exchange in cells, including prokaryotic cells and eukaryotic cells. In some embodiments, a gene editing complex is delivered to a eukaryotic cell. Examples of eukaryotic cells include but are not limited to mammalian cells, insect cells, plant cells, and fungal cells. In some embodiments, the cell is a mammalian cell. In some embodiments the mammalian cell is a human cell, feline cell, canid cell, non-human primate cell, or rodent cell (e.g., mouse cell, rat cell, guinea pig cell, pig cell etc.). In some embodiments, the cell is a somatic cell. "Somatic cell" refers to any cell (e.g., a diploid cell) other than a gamete, germ cell, gametocyte.

In some embodiments, the cell is in a subject. In some embodiments, the subject is a mammal. In some embodiments, the subject is selected from a mouse, a rat, a rabbit, a dog, a cat, a sheep, a pig, and a non-human primate. In some embodiments, the subject is a human. In some embodiments, the subject has or is at risk of having a disease, optionally a monogenic recessive disorder. Examples of monogenic recessive disorders include but are not limited to phenylketonuria (PKU), tyrosinemia, lysosomal storage disorder (e.g., Tay-Sachs disease, GM1 gangliosidosis, Sandhoff disease, etc.), a sickle-cell syndrome, Hurler syndrome, Canavan disease, and cystic fibrosis.

Generally, methods of the disclosure are useful for targeted allelic exchange in any cellular environment, e.g., in vitro, ex vivo, or in vivo. For example, in some embodiments, a cell (e.g., a somatic cell) is removed from a subject and at least one component of a gene editing complex as described by the disclosure is delivered to the cell. In some embodiments, the cell is reintroduced into the subject after being contacted with the gene editing complex (e.g., ex vivo therapy). In some embodiments, at least one component of a gene editing complex is administered to a subject (e.g., in vivo therapy). In some embodiments, the at least one component of the recombinant gene editing complex is administered to a subject by injection.

Pharmaceutical Compositions

In some aspects, the disclosure relates to compositions comprising at least one component of a gene editing complex (e.g., a rAAV comprising at least one component of a gene editing complex) as described by the disclosure. In some embodiments, compositions comprising at least one component of a gene editing complex as described herein are delivered to a subject in need thereof. The at least one component of a gene editing complex may be delivered to a subject in compositions according to any appropriate methods known in the art. It should be appreciated that compositions may comprise one or more (e.g., a plurality) of components as described by the disclosure. In some embodiments, a plurality of components is 2, 3, 4, 5, 6, 7, 8, 9, 10, or more components. In some embodiments, the composition further comprises a pharmaceutically acceptable carrier.

Suitable carriers may be readily selected by one of skill in the art. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the at least one component of a gene editing complex and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The at least one component of a gene editing complex is administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of composition (e.g., composition comprising at least one component of a gene editing complex) required to achieve a particular "therapeutic effect," will vary based on several factors including, but not limited to: the route of administration, the level of gene or RNA expression required to achieve a therapeutic effect, the specific disease or disorder being treated, and the stability of the gene or RNA product. One of skill in the art can readily determine a dose range to treat a patient having a particular disease or disorder based on the aforementioned factors, as well as other factors that are well known in the art.

Dosage regime may be adjusted to provide the optimum therapeutic response. For example, the at least one component of a gene editing complex may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject compositions, whether the compositions are to be administered to cells or to subjects.

Formulation of pharmaceutically-acceptable excipients and carrier solutions is well-known to those of skill in the art, as is the development of suitable dosing and treatment regimens for using the particular compositions described herein in a variety of treatment regimens.

Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver at least one component of a gene editing complex in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver nucleic acids. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the nucleic acid in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present disclosure into suitable cells. In particular, the nucleic acids may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587). Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 ANG., containing an aqueous solution in the core.

Alternatively, nanocapsule formulations of the composition may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use. In addition to the methods of delivery described above, the following techniques are also contemplated as alternative methods of delivering the compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Modes of Administration

In some embodiments, at least one component of a gene editing complex is delivered to a cell (e.g., administered to a patient in need thereof) as a recombinant adeno-associated virus (rAAV). The at least one component can be fused to the capsid protein (e.g., VP2) of the rAAV, encoded as a transgene in an rAAV vector (e.g., a transgene encoding a gRNA or sgRNA), or a combination of the foregoing.

rAAVs may be delivered to a subject in compositions according to any appropriate methods known in the art. The rAAV, preferably suspended in a physiologically compatible carrier (e.g., in a composition), may be administered to a subject, e.g., host animal, such as a human, mouse, rat, cat, dog, sheep, rabbit, horse, cow, goat, pig, guinea pig, hamster, chicken, turkey, or a non-human primate (e.g., Macaque). In some embodiments, a host animal is a human. In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

Aspects of the instant disclosure relate to compositions comprising a recombinant AAV comprising a capsid protein having a terminally grafted nuclease (e.g., at least one component of a gene editing complex). In some embodiments, the nuclease is terminally grafted onto a capsid protein. In some embodiments, the a terminally grafted nuclease is present on all three capsid proteins (e.g., VP1, VP2, VP3) of the rAAV. In some embodiments, the terminally grafted nuclease is present on two of the capsid proteins (e.g., VP2 and VP3) of the rAAV. In some embodiments, the terminally grafted nuclease is present on a single capsid protein of the rAAV. In some embodiments, the terminally grafted nuclease is present on the VP2 capsid protein of the rAAV. In some embodiments, the composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes (e.g., encoding different gRNA or sgRNA, or multiple copies of a gRNA or sgRNA).

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

EXAMPLES

Example 1

Figure 6A:
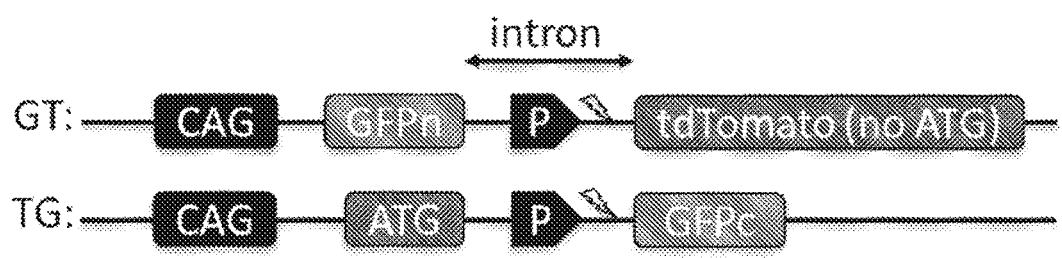
FIGS. 6A-6B show in vivo allele exchange in GT/TG reporter mice following adult treatment.

In this example, delivery of a gene editing complex that generates DNA double-stranded breaks at the same location on two alleles was tested. A gene editing complex (e.g., SpCas9) targeting a knock-in mouse model that carries GFP$^{N\text{-}term}$-intron-tdTomato$^{C\text{-}term}$ and tdTomato$^{N\text{-}term}$-intron-GFP$^{C\text{-}term}$ expression cassettes, respectively, at the same genomic location on each copy of Chr 11 was produced (FIG. 6A). The GT construct (half GFP-intron-tdTomato without ATG) or the TG construct (ATG-intron-half GFP) is carried on the same locus of Chromosome 11. Both constructs share the same intronic sequence containing a loxP site (P). GT homozygous and TG homozygous mice were bred to obtain GT/TG compound heterozygous mice. CAG: CAG promoter; lightning: sgIntron target site.

In this model, allelic exchange at the intronic region reconstitutes the full-length GFP and tdTomato, serving as a reporter system. Cre serves as positive control, which mediates recombination of the GT and TG alleles yielding GFP and tdTomato expression.

Recombinant AAV (rAAV) vectors expressing SpCas9 and sgRNA targeting the intron was administered to adult mice by tail vein injection. Specifically, 6-week-old GT/TG mice were treated by tail vein injection with rAAV9.CB6-PI-Cre (Cre) at 2E12 genome copies (GC), or rAAV9.u1a-SpCas9 combined with rAAV9.u6-sgIntron (Cas9+sgIntron) at 1E12 GC of each vector. 5 weeks later, fluorescence signal of GFP (green) and tdTomato (red) was examined in cryo-sections of liver and heart.

Figure 6B:
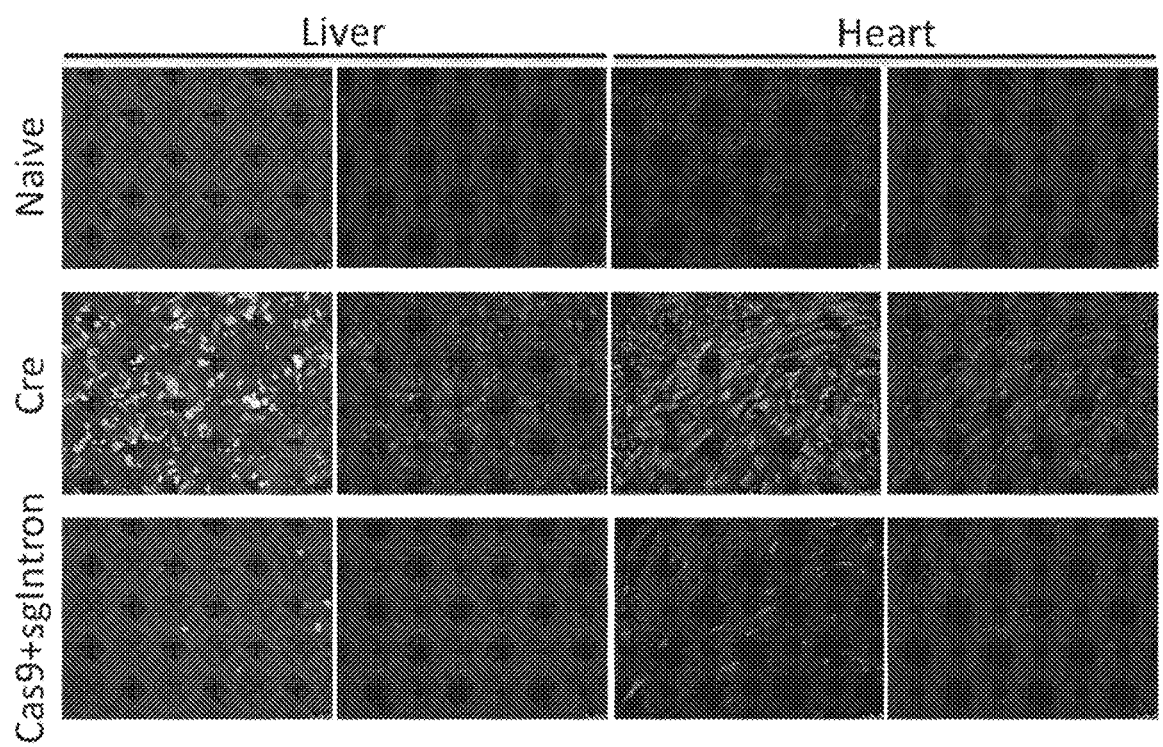

Results indicate that GFP and tdTomato fluorescence were observed in cryosections of peripheral tissues including liver and heart (FIG. 6B), whereas there was no such fluorescence observed in the tissue samples from untreated mice, demonstrating that allele exchange occurred, and that the reconstituted alleles yielded protein expression.

The same experiment as described above was also performed in neonatal (P1) mice. Neonatal (postnatal day 1, P1) GT/TG mice were treated by facial vein injection with rAAV9.CB6-PI-Cre (Cre) at 4E11 genome copies (GC), or rAAV9.u1a-SpCas9 combined with rAAV9.u6-sgIntron (Cas9+sgIntron) at 2E11 GC of each vector. 5 weeks later, fluorescence signal of GFP (green) and tdTomato (red) was examined in cryo-sections of liver and heart. GFP and tdTomato fluorescence were observed in cryosections of peripheral tissues including liver and heart (FIG. 6B), whereas there was no such fluorescence observed in the tissue samples from untreated mice, demonstrating that allele exchange occurred (FIG. 7).

Figure 7A:
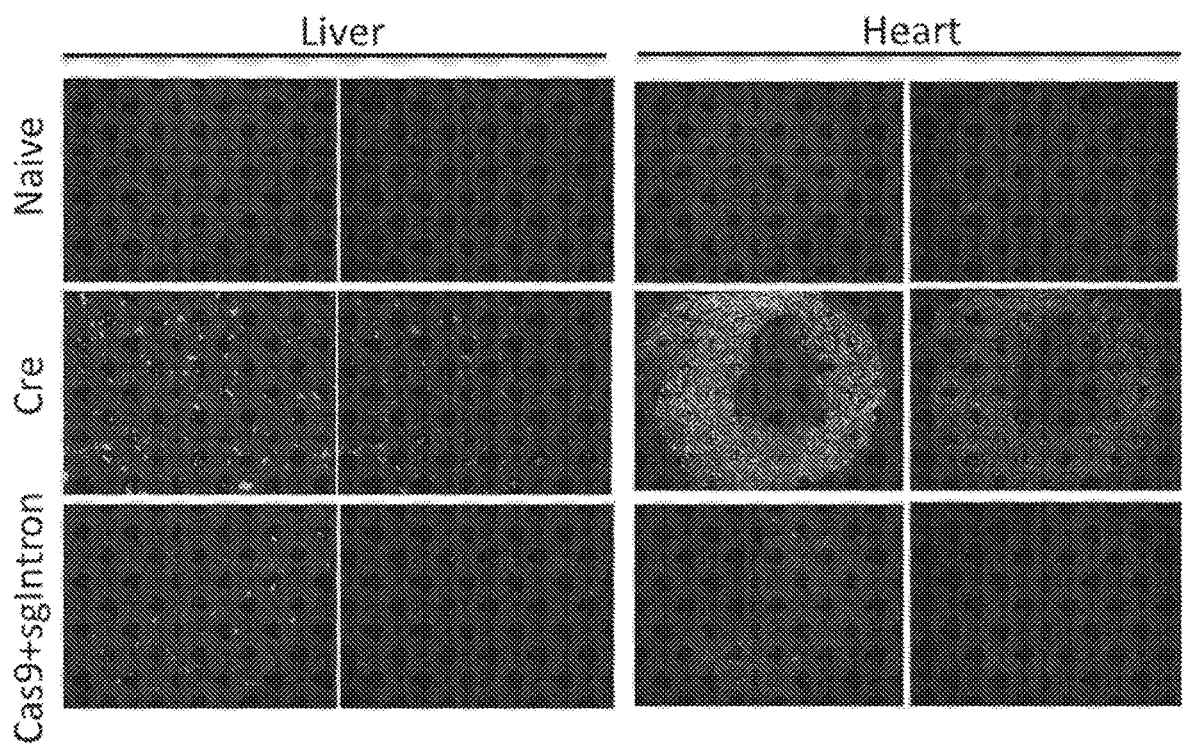
FIGS. 7A-7D show nuclease-mediated allelic exchange in the GT-TG mice.
Figure 7B:
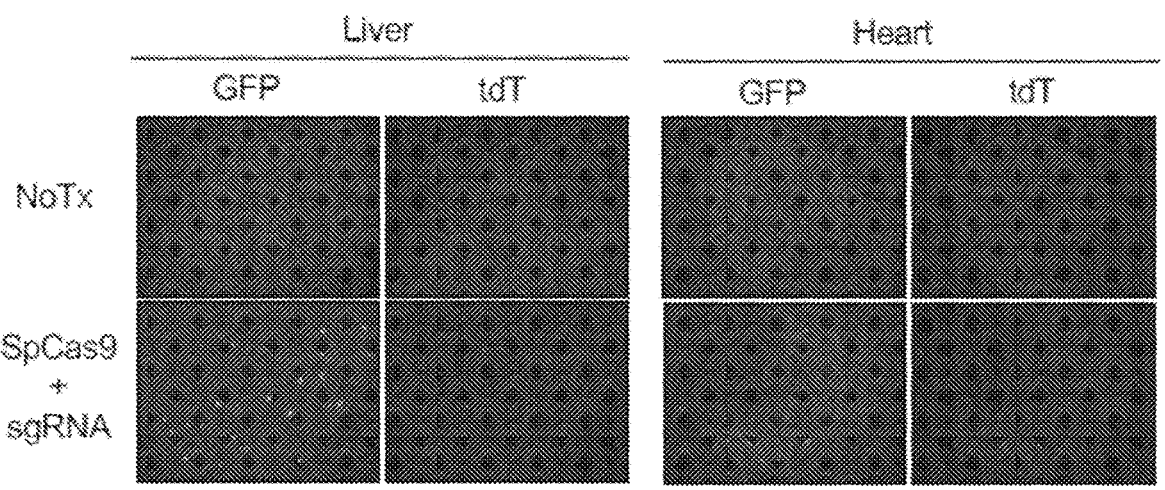
Figure 7C:
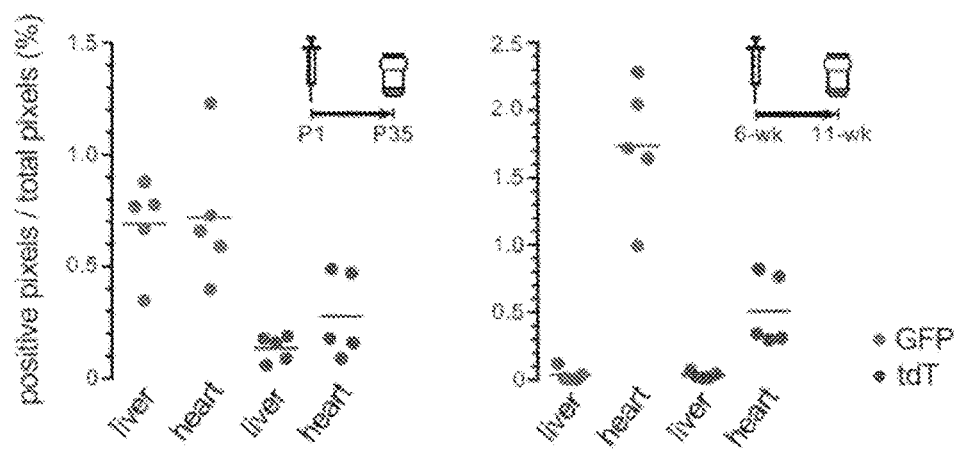
Figure 7D:
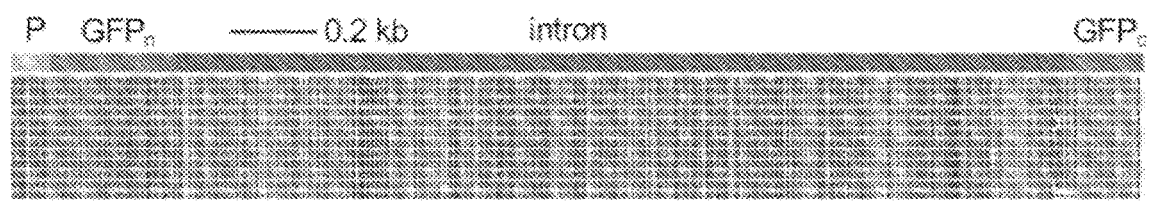

In another example, GT-TG mice were treated with a mixture of rAAV9-SpCas9 and rAAV9-sgRNA at two different ages (n=5 group)-postnatal day 1 (P1) or six weeks old- and fluorescence in tissue sections was examined five weeks after treatment (FIG. 7B). The percentage of fluorescence in liver and heart in these two experiments was quantified (FIG. 7B). Long-range PCR and single-molecule, real time (SMRT) sequencing, was performed and the presence of GG allele resulting from allelic exchange in the treated mouse liver was observed (FIG. 7D and Table 1).

TABLE 1

| Sample | TG reads | GG reads | Exchange frequency |
|---|---|---|---|
| NoTx | 11136 | 0 | 0 |
| SpCas9 + sgRNA | 10084 | 12 | 0.12% |

In sum, co-delivery of SpCas9 and sgIntron results in GFP and tdTomato expression in both liver and heart, demonstrating that allele exchange occurred following Cas9/sgRNA-induced double-stranded breaks and DNA repair in both adult and neonatal mice.

Example 2

In this example, a novel approach to repairing recessive compound heterozygous mutations is described. In contrast to the two existing therapeutic gene editing strategies mentioned above, DNA double-stranded breaks (DSBs) were used to induce exchange of DNA sequence between the two mutant alleles (e.g., each allele having mutation(s) that cause or are associated with disease), so that one exchanged allele carries two (or more) mutations, whereas the other exchanged allele carries no mutation (FIG. 1). After allelic exchange mediated by methods described in this disclosure, normal gene expression takes place from the reconstituted, mutation-free exchanged allele, which alleviates the disease phenotype.

The strategy described by the disclosure is suitable for repairing recessive compound heterozygous mutations that are separated by at least one intronic sequence. For example, DSBs are induced in an intron between the two mutation sites, which will be followed by chromosomal exchange to reconstitute the mutation-free allele. DSBs are strategically induced in intron because small insertion/deletion (indel) changes at the DSB that are potentially introduced during chromosomal exchange will likely not affect normal gene expression. CRISPR/Cas9-based gene editing is described in this example, although other methods such as zinc-finger nuclease- and TALEN-based gene editing strategies can also serve the same purpose.

Figure 2:
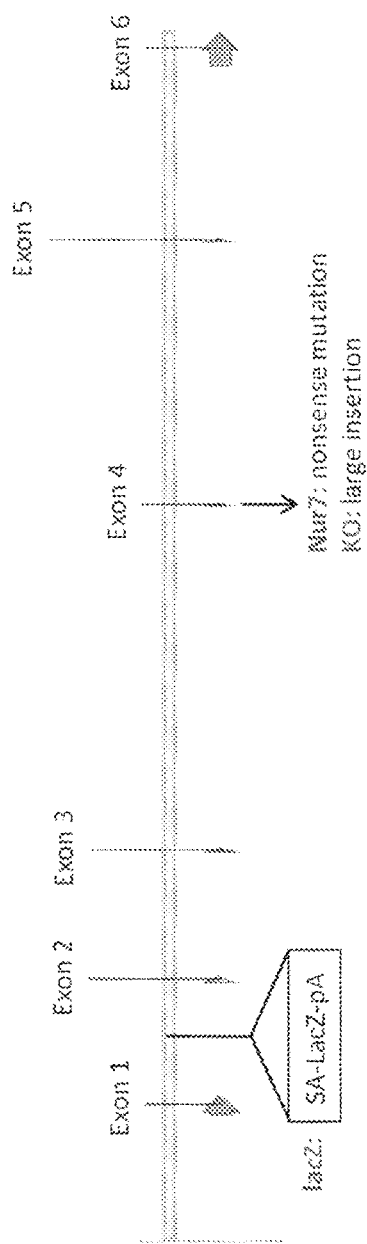
FIG. 2 shows mouse Aspa gene structure and disease-causing mutations. Mutation position and type are labeled and denote three mouse models of Canavan disease. The lacZ model of Canavan disease has a mutation in intron 1. Mutations causing disease in the Nur7 (nonsense mutation) and KO (large insertion) models are both in exon 4. SA: splicing acceptor. pA: polyadenylation signal.

Mice carrying compound heterozygous mutations of the Aspa gene were obtained. Aspa deficiency is the cause of Canavan disease (CD), a type of leukodystrophy mainly affecting brain white matter. Three CD mouse models carrying three different mutations are available, namely the lacZ, the Nur7 and the KO models (FIG. 2A). The lacZ model carries an insertion in intron 1 of Aspa gene, and the insertion contains a polyadenylation signal that prematurely terminates transcription of the Aspa locus. The Nur7 model carries a nonsense mutation in exon 4. The KO model carries a disruptive (e.g., large) insertion in exon 4.

Figure 3A:
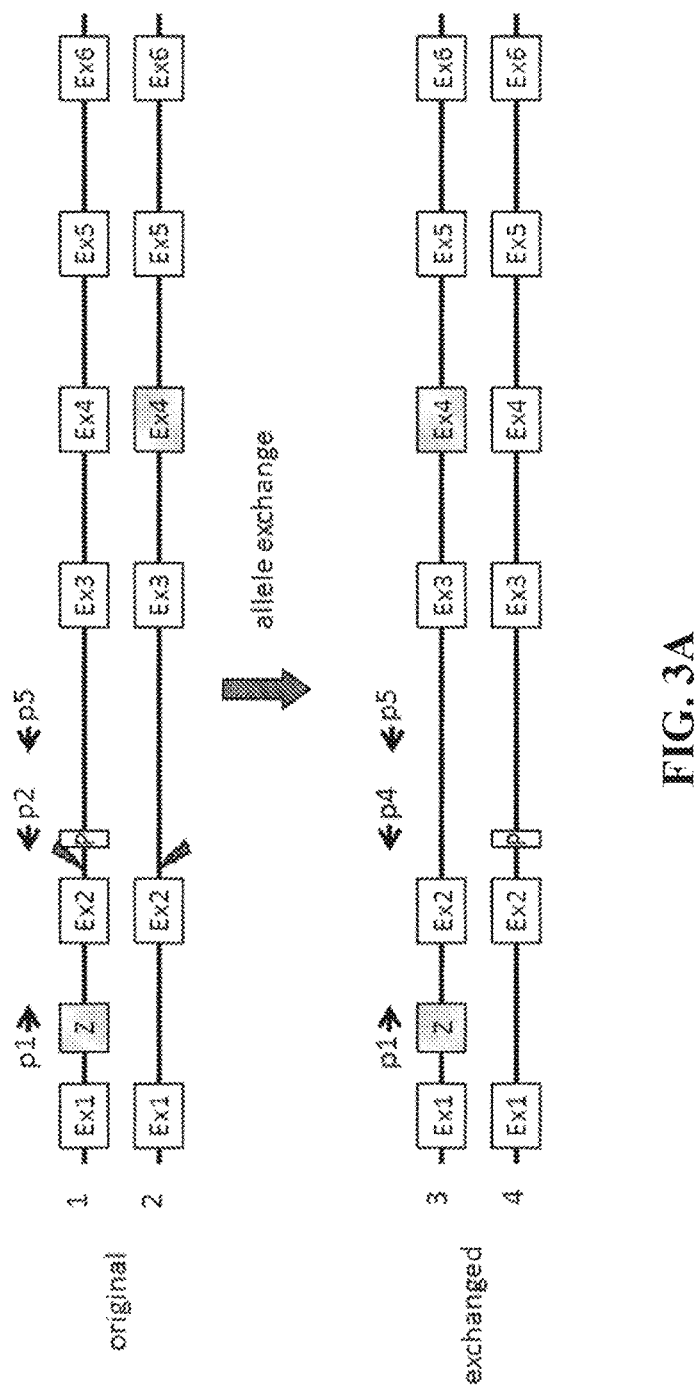
FIGS. 3A-3B show strategies to examine whether allele exchange can occur in mouse tissue (e.g., mouse liver).
Figure 3B:
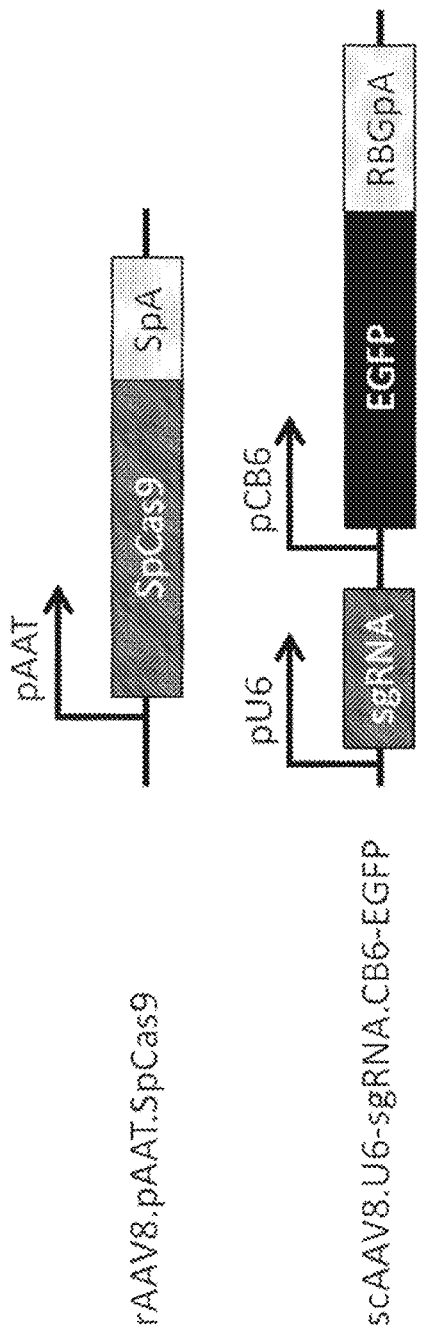

For this study, lacZ/Nur7 and lacZ/KO mice were obtained through breeding (FIG. 2B). The lacZ allele also carries a loxP site in intron 2, which serves as a landmark to assess chromosomal exchange by nested PCR (FIG. 3A). A sgRNA targeting a region between exon 2 and the loxP site in intron 2 was designed (FIG. 3A). The sgRNA targeting site is present in all three mutant Aspa alleles. Two rAAV vectors were packaged to deliver SpCas9 and sgRNA separately (FIG. 3B). Tail vein injection of the two vectors ($8 \times 10^{11}$GC each vector) to 6-week-old lacZ/Nur7 and lacZ/KO mice was performed. Mice that were not treated served as control.

Figure 4:
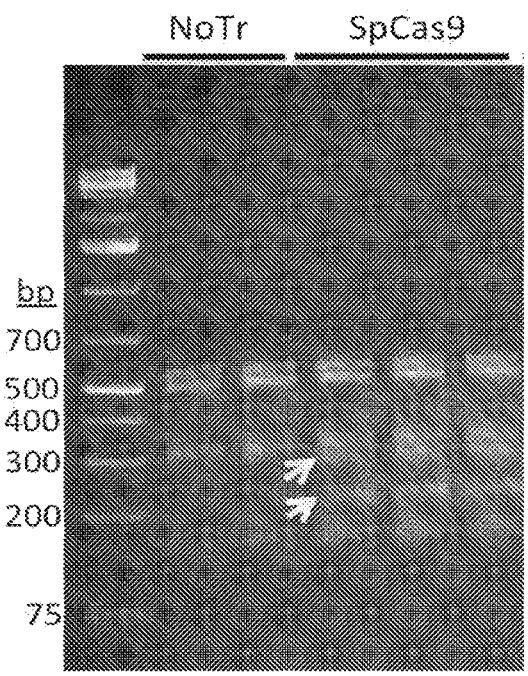
FIG. 4 shows CRISPR/Cas9 design induced indel mutations in mouse tissue (e.g., mouse liver). SURVEYOR assay shows positive bands (arrows), suggesting indel mutations after gene editing. The two bands of about 500 bp are initial PCR products from the original compound heterozygous alleles. The larger band represents the lacZ allele because it has an extra loxP insertion. NoTr: no treatment. Each lane represents an individual mouse.

Three weeks after injection, the mice were euthanized, the liver was harvested, and total DNA was extracted. A SURVEYOR assay first was performed to confirm that the SpCas9 and sgRNA induced gene editing (FIG. 4).

Figure 5A:
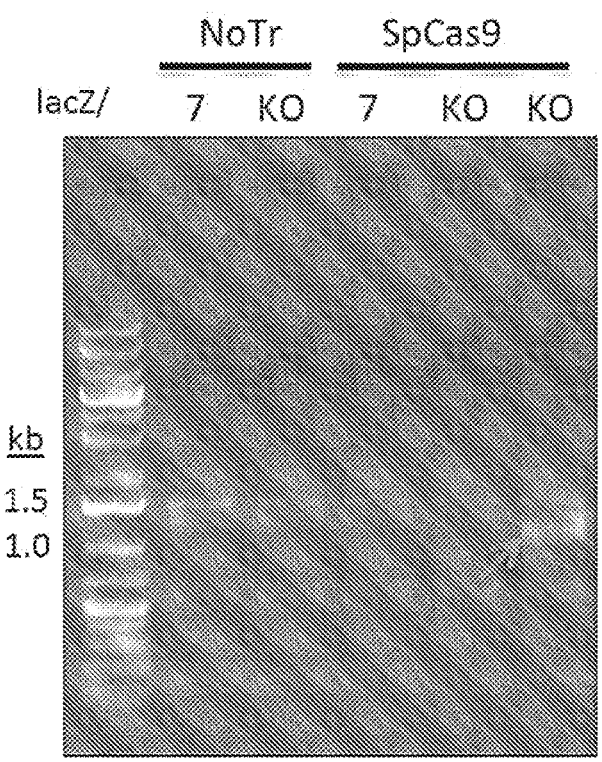

Nested PCR for the exchanged allele indicated a band that is consistent with the predicted size (FIG. 5A). TOPO sequencing confirmed that this PCR product species contained the full length PCR product harboring both a sequence that is only present in the lacZ allele, and a sequence that is only present in the Nur7 or the KO allele (FIG. 5B), thus demonstrating that the chromosomal exchange occurred. In addition, TOPO sequencing detected indel mutations at the predicted SpCas9 cleavage site (FIG. 5B), indicating that the chromosomal exchange was repaired through the error-prone NHEJ pathway. It is worth noting that the small indels are within intronic sequence and does not seem to affect mRNA splicing.

Single molecule, high-throughput DNA sequencing (PacBio sequencing, NextSeq sequencing) to quantitatively examine the frequency of chromosomal exchange is performed. Meanwhile, in some embodiments, this strategy is assessed in compound heterozygous cell lines derived from patients affected by CD and other diseases, such as Mucopolysacchridosis type I-Hurler syndrome.

Example 3

In this example, it was confirmed that allelic exchange is a viable therapeutic approach in compound heterozygous (comp het) mice of hereditary tyrosinemia type I (HT1), a recessive metabolic disease caused by mutations in the FAH gene. Bi-allelic FAH gene disruption leads to incomplete degradation of tyrosine, and accumulation of toxic intermediate metabolites that results in liver dysfunction. NTBC is a compound that can block an earlier step in the tyrosine degradation pathway, and therefore reduces the formation of the toxic intermediate metabolites and relieves symptoms.

Figure 8A:
FIGS. 8A-8G show functional recovery in compound heterozygous hereditary tyrosinemia type I (HT1) mice after nuclease-mediated allelic exchange.

Two HT1 mouse models homozygous for two different Fah mutant alleles, namely the Fah$^{\Delta E5}$ allele and the Fah$^{PM}$ allele, were obtained and comp het HT1 mice carrying both alleles were generated (FIG. 8A). A sgRNA targeting Fah intron 7 (sgFah) (FIG. 8A) was produced. A sgRNA targeting an intron of the Aspa gene (sgAspa) was produced as a control.

Figure 8B:
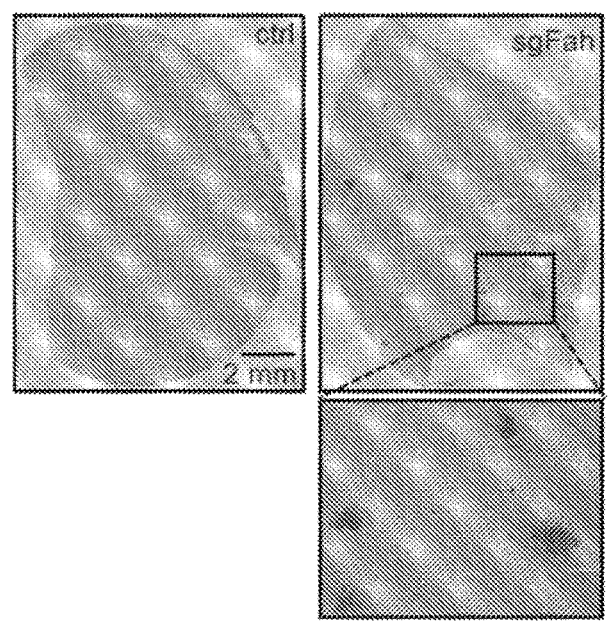
Figure 8C:
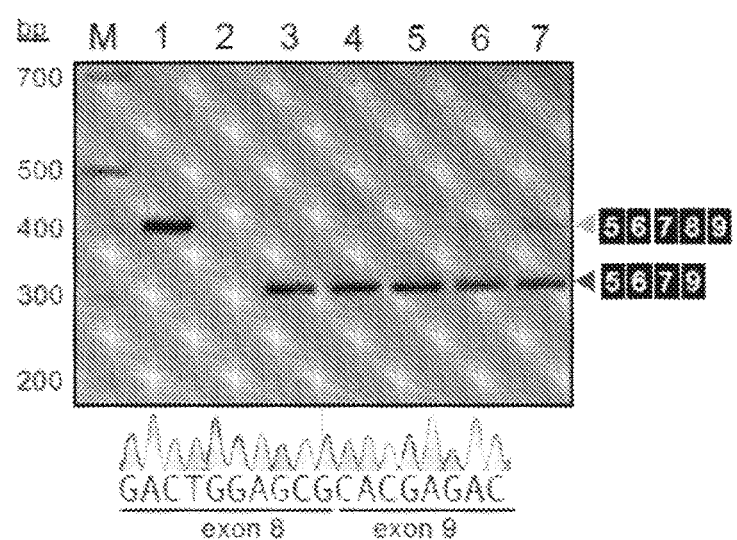
Figure 8D:
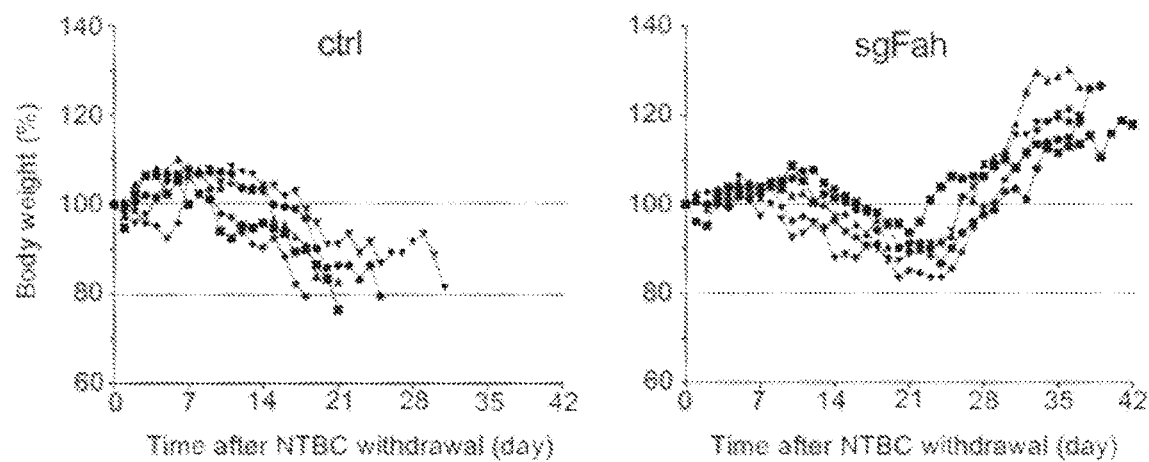

Comp het HT1 mice were treated with rAAV9-SpCas9 and rAAV8-sgFah (sgFah), or rAAV9-SpCas9 and rAAV8-sgAspa (ctrl) at P1, and maintained on NTBC water. Five weeks later, Fah-positive cells were observed in the sgFah liver sections by immunohistochemistry (IHC) (FIG. 8B); normal Fah transcript was observed in the sgFah liver lysate by reverse transcription PCR (FIG. 8C). When NTBC was removed from the drinking water at P35, mice in the ctrl group lost ~20% body weight within 4.5 weeks due to liver dysfunction, and had to be euthanized (FIG. 8D). In contrast, mice in the sgFah group recovered from the initial weight loss, and eventually gained weight (FIG. 8D).

Figure 8E:
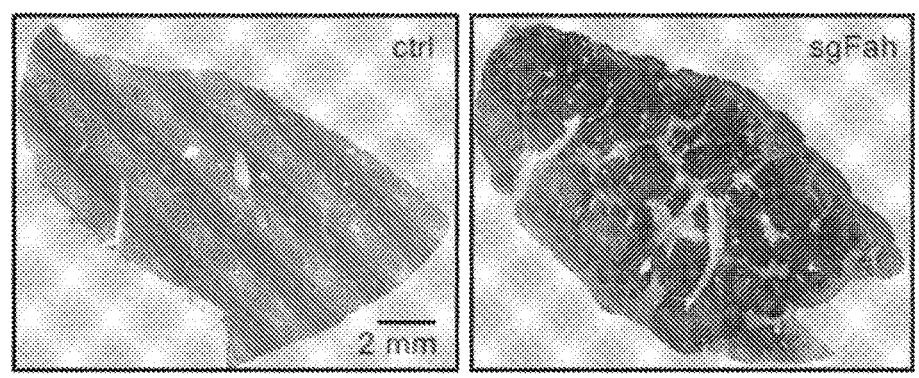
Figure 8F:
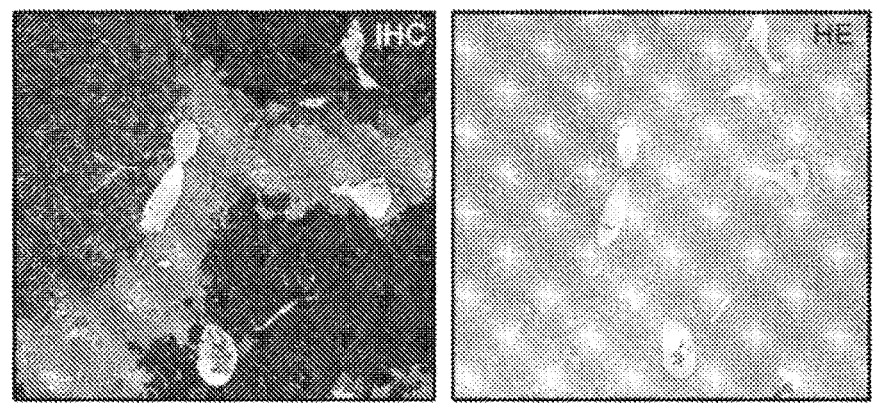
Figure 8G:
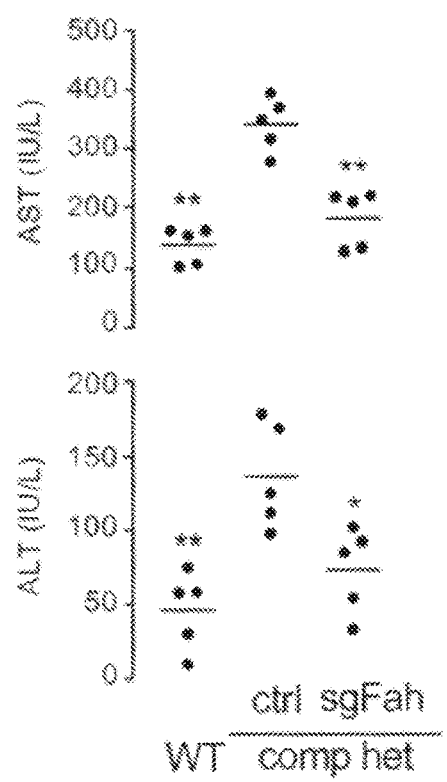

When mice in the sgFah group were euthanized after weight recovery and examined by IHC, massive populations of Fah-positive cells were observed (FIG. 8E), which is consistent with the observed growth advantage of Fah-expressing hepatocytes over Fah-null cells. The Fah-positive cells appear to be normal as assessed by histological staining (FIG. 8F). While mice in the ctrl group had elevated transaminases compared to wild-type mice indicating liver damage, treatment with sgFah normalized this disease-related phenotype (FIG. 8G). Together, these data indicate that allelic exchange in the comp het HT1 mice results in functional correction of disease-related phenotypes.

Figure 9A:
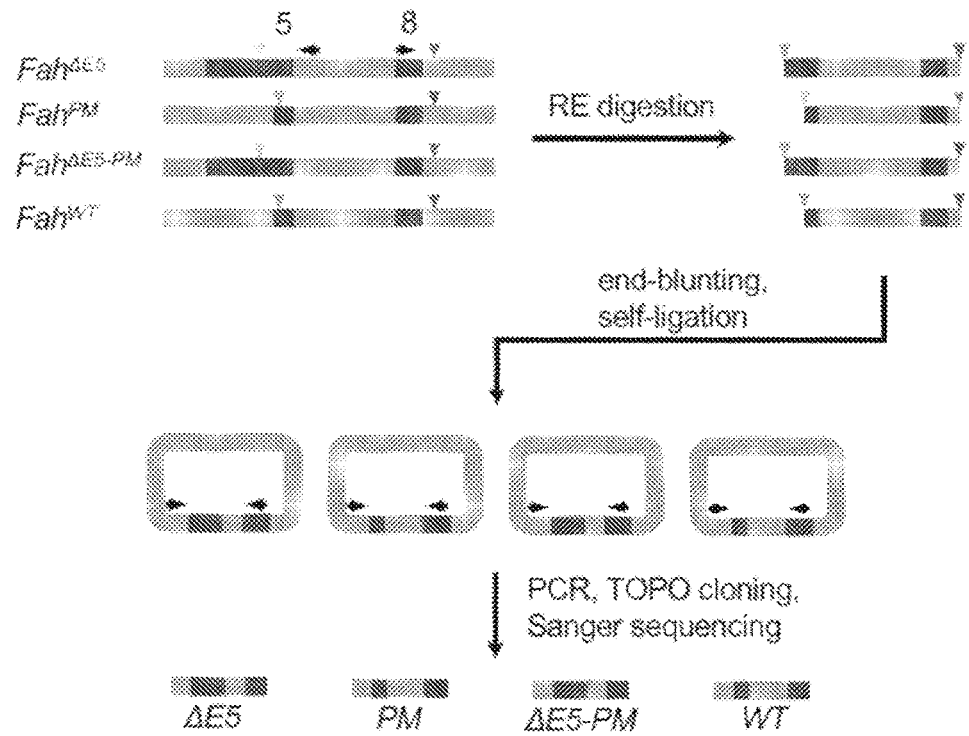
FIGS. 9A-9B show molecular demonstration of allelic exchange in comp het HT1 mice.
Figure 9B:
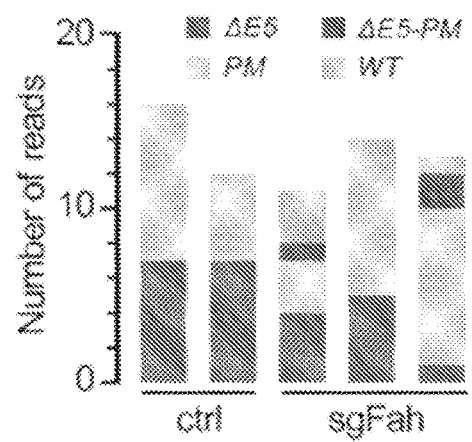

Furthermore, the occurrence of allelic exchange in the sgFah mouse liver at the genomic DNA level was observed using a circularization PCR method (FIG. 9A). Data indicated that the Fah$^{\Delta E5-PM}$ and Fah$^{WT}$ alleles resulting from allelic exchange were detected only in the sgFah group, but not in the ctrl group.

| SEQUENCES |
|---|
| >SEQ ID NO: 1 nucleic acid sequence<br>GAGGTATTGTACAAAGATACAGAGGCAGTGATGAT |
| >SEQ ID NO: 2 nucleic acid sequence<br>GAGGTATTGTACACAGAGGCAGTGATGAT |
| >SEQ ID NO: 3 nucleic acid sequence<br>GAGGTATTGTACAAAAGAGGCAGAGGCAGTGATGAT |
| >SEQ ID NO: 4 nucleic acid sequence<br>GACTGGAGCGCACGAGAC |
| >SEQ ID NO: 5 sg-Intron (sgRNA target site 5'→3')<br>GGGTGGGAAAATAGACCAAT |
| >SEQ ID NO: 6 sgFah (sgRNA target site 5'→3')<br>AAAGAGTGGAGCCTTAGTGT |
| >SEQ ID NO: 7 sgAspa (sgRNA target site 5'→3')<br>GGTATTGTACAAAGATACAG |

This disclosure is not limited in its application to the details of construction and the arrangement of components set forth in this description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. A method comprising contacting a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each of the two chromosomes at an intronic site aligning between the positionally unique mutations to produce a mutation-free chromosome and a mutant chromosome via non-homologous end-joining (NHEJ); wherein the recombinant gene editing complex comprises a Cas protein, and a guide RNA (gRNA) or single-stranded guide RNA (sgRNA) that is complementary to SEQ ID NOs: 6 or 7.

2. The method of claim 1, wherein the position of each heterogeneous recessive allele is separated by at least one complete intron.

3. The method of claim 2, wherein the complete intron is at least 50 nucleotides in length.

4. The method of claim 1, wherein each heterogeneous allele comprises a polymorphism selected from a single nucleotide polymorphism (SNP), an insertion polymorphism, or a deletion polymorphism.

5. The method of claim 4, wherein the polymorphism is associated with a disease.

6. The method of claim 5, wherein the disease is selected from the group consisting of tyrosinemia and Canavan disease.

7. The method of claim 1, wherein the Cas protein is a Cas9 protein or a Cpf1 protein.

8. The method of claim 1, wherein the method comprises contacting the pair of homologous chromosomes in a cell.

9. A method comprising delivering to a cell at least one component of a recombinant gene-editing complex, the cell having a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each of the two chromosomes at an intronic site aligning between the positionally unique mutations to produce a mutation-free chromosome and a mutant chromosome via non-homologous end-joining (NHEJ); wherein the recombinant gene-editing complex comprises a Cas protein, and a guide RNA (gRNA) or single-stranded guide RNA (sgRNA); and wherein the gRNA or sgRNA is complementary to SEQ ID NOs: 6 or 7.

10. The method of claim 9, wherein the cell is in a subject.

11. The method of claim 9, wherein the cell is in vitro or ex vivo.

12. The method of claim 9, wherein the at least one component of the gene editing complex is delivered to the cell in a recombinant adeno-associated virus (rAAV).

13. A method comprising administering to a subject at least one component of a recombinant gene-editing complex, the subject having a cell comprising a pair of homologous chromosomes, each chromosome of the pair having a heterogeneous recessive allele of the same gene, each heterogeneous recessive allele having a positionally unique mutation, with a recombinant gene editing complex, under conditions under which the recombinant gene editing complex induces double stranded breaks in each of the two chromosomes at an intronic site aligning between the positionally unique mutations, wherein the administered gene-editing complex enters the cell and produces a mutation-free chromosome and a mutant chromosome in the cell via non-homologous end-joining (NHEJ); wherein the recombinant gene-editing complex comprises a Cas protein, and a guide RNA (gRNA) or single-stranded guide RNA (sgRNA); and wherein the gRNA or sgRNA is complementary to SEQ ID NOs: 6 or 7.

14. The method of claim 13, wherein the at least one component of the recombinant gene editing complex is administered to the subject by injection.

15. The method of claim 13, wherein the subject is a mammal.

* * * * *